(12) United States Patent
Smith et al.

(10) Patent No.: US 10,668,002 B2
(45) Date of Patent: Jun. 2, 2020

(54) ANHYDROUS POLYSACCHARIDE FILMS

(71) Applicant: REGENESIS GROUP, East Harwich, MA (US)

(72) Inventors: James Smith, East Harwich, MA (US); George Kellett, Cranford, NJ (US)

(73) Assignee: ReGenesis Group, East Harwich, MA (US)

( * ) Notice: Subject to any disclaimer, the term of this patent is extended or adjusted under 35 U.S.C. 154(b) by 0 days.

(21) Appl. No.: 16/221,328

(22) Filed: Dec. 14, 2018

(65) Prior Publication Data
US 2019/0216710 A1    Jul. 18, 2019

Related U.S. Application Data

(60) Provisional application No. 62/618,805, filed on Jan. 18, 2018.

(51) Int. Cl.
*A61K 8/81* (2006.01)
*A61K 8/891* (2006.01)
*A61K 8/894* (2006.01)
*A61Q 19/02* (2006.01)
*A61K 8/73* (2006.01)
*A61K 8/88* (2006.01)
*A61K 8/85* (2006.01)
*A61K 8/893* (2006.01)
*A61Q 9/02* (2006.01)
*A61Q 9/04* (2006.01)
*A61K 8/02* (2006.01)
*A61L 26/00* (2006.01)
(Continued)

(52) U.S. Cl.
CPC .............. *A61K 8/73* (2013.01); *A61K 8/0204* (2013.01); *A61K 8/0216* (2013.01); *A61K 8/8158* (2013.01); *A61K 8/85* (2013.01); *A61K 8/88* (2013.01); *A61K 8/893* (2013.01); *A61K 9/0014* (2013.01); *A61K 47/06* (2013.01); *A61K 47/10* (2013.01); *A61K 47/32* (2013.01); *A61K 47/34* (2013.01); *A61K 47/36* (2013.01); *A61L 26/00* (2013.01); *A61Q 9/02* (2013.01); *A61Q 9/04* (2013.01); *A61Q 19/00* (2013.01); *C11D 17/06* (2013.01); *A61K 2800/10* (2013.01); *A61K 2800/31* (2013.01); *B26B 21/443* (2013.01)

(58) Field of Classification Search
None
See application file for complete search history.

(56) References Cited

U.S. PATENT DOCUMENTS

| | | | |
|---|---|---|---|
| 4,462,981 | A | 7/1984 | Smith |
| 4,690,821 | A | 9/1987 | Smith |

(Continued)

FOREIGN PATENT DOCUMENTS

| | | |
|---|---|---|
| WO | WO 97/02116 | 1/1997 |
| WO | WO 2007/016394 | 2/2007 |
| WO | WO 2016/054167 | 4/2016 |

*Primary Examiner* — Kyung S Chang
(74) *Attorney, Agent, or Firm* — Nash and Titus, LLC

(57) ABSTRACT

This invention relates to anhydrous polymer film compositions containing various polysaccharide ingredients useful for numerous applications. The invention relates to anhydrous liquid compositions that, when dried down, form a film that can release desired ingredients in a controlled and extended-use way. The films can be erodible, partially soluble or completely soluble when used in conjunction with water or water vapor.

14 Claims, 2 Drawing Sheets

(51) Int. Cl.
*A61K 47/06* (2006.01)
*A61K 9/00* (2006.01)
*C11D 17/06* (2006.01)
*A61Q 19/00* (2006.01)
*A61K 47/10* (2017.01)
*A61K 47/36* (2006.01)
*A61K 47/34* (2017.01)
*A61K 47/32* (2006.01)
*B26B 21/44* (2006.01)

(56) References Cited

U.S. PATENT DOCUMENTS

| | | | |
|---|---|---|---|
| 5,588,732 A | 7/1996 | Smith | |
| 6,001,380 A | 12/1999 | Smith | |
| 2012/0134942 A1* | 5/2012 | Thomaides | C02F 5/10 |
| | | | 424/59 |
| 2013/0289080 A1* | 10/2013 | Masse | A61K 8/8152 |
| | | | 514/345 |

* cited by examiner

ANHYDROUS POLYSACCHARIDE FILMS

TECHNICAL FIELD

This invention relates to anhydrous polymer film compositions containing various polysaccharide ingredients useful for numerous applications. The films can be erodible, partially soluble or completely soluble when used in conjunction with water or water vapor.

BACKGROUND OF THE INVENTION

The background of this invention is related to the field of shaving; however, during the development of this invention, it was determined modifications in the selection of active ingredients would broaden use to include skin care, hair care, dermatology, drug delivery, wound care, fabric softeners, hydrophilic polyurethane foams and solid laundry detergents.

There are a variety of shaving materials and implements for use on skin. For example, razors used in conjunction with shave creams not only contain blades for removal facial hair, but contain strips at the top of a cartridge or razor for releasing lubricious ingredient such as polyethylene oxide making the shaving experience smoother and more comfortable when wetted.

These razors or cartridges that contain these so called "comfort strips" are usually made by incorporating high molecular weight polyethylene oxide polymer (PEO) in various plastics via high temperature extrusion or injection molding. The difficulty with these strips is they have limited function in releasing the (PEO) polyethylene oxide when wetted during the shaving experience. The PEO functions in a time release mode but usually lasts for only 5 to 7 shaves. Moreover, there is little additional benefit to the skin during the shaving experience from these strips. The high temperature method of manufacture limits the kinds and amount of other skin care ingredients that can be incorporated.

As a result of these observations, there is a need for a new lubricious shaving ingredient(s) other than PEO and a solid system where a variety of skin care and other ingredients can be included and dispensed on a variety of surfaces.

SUMMARY OF THE INVENTION

This invention is based on the discovery that the combination of certain ingredients in an anhydrous solvent forms an anhydrous liquid composition that, when dried down, forms a film that can release desired ingredients in a controlled and extended-use way—addressing the problems identified above. The novelty of the invention is very high levels of polysaccharides can be dispersed in anhydrous fluid compositions and when dried release a very lubricious action on surfaces in a controlled manner when exposed to water or water vapor. The invention also has other advantages described below.

Specifically, in one embodiment, this invention entails an anhydrous fluid composition containing at least one base polymer group (BPG), at least one polysaccharide, and an anhydrous solvent. By "anhydrous composition" it is meant no or only trace amounts of water or water vapor is present in the fluid anhydrous composition. Water is undesirable because it can react with the polysaccharide component (especially polysaccharides like CMC). Therefore, water cannot be present in an amount that it would react with polysaccharide, and interfere with the function of the polysaccharide as described herein.

Optionally, one or more additional ingredients may be included which are releasable from the film that is the dried-down product of the liquid composition. These additional ingredients should not interfere with the anhydrous character of the fluid composition, or the interaction of the BPG and the polysaccharide, or the ability of the fluid to form a solid film when dried. For instance, additional ingredients may include various skin care ingredients useful for residual skin feel, or those useful for improving shaving, or having medicinal or cleansing properties. Other ingredients such as proteins, starches, phytosterols, ceramides, proteins, and other hydrocolloids can be included as well. A detailed description of such additional ingredients is below.

In a second embodiment, the invention entails a film that contains at least one base polymer group (BPG), at least one polysaccharide, and optionally one or more ingredients that are releasable from the film. As noted above, the additional ingredients should not interfere with the anhydrous character of the fluid composition, or the interaction of the BPG and the polysaccharide, or the ability of the fluid to form a solid film when dried. This film is the result of drying down, or otherwise removing the anhydrous solvent from the above-described liquid composition. The solid film preferably should be tack free, flexible, capable of being coated on surfaces and cast into various thicknesses.

It should be noted that the combination of BPG and polysaccharide alone provides benefits, even in the absence of other ingredients. For instance, this combination alone when dried to form a film provides an unusual lubricious action when wetted or used on wet skin. This combination can also be used as a platform for the release of a wide variety of ingredients when used with water or water vapor.

In another embodiment, our invention entails multiple uses and applications of the liquid and, especially, the film. The methods are described in further detail below.

The base polymer group (BPG) may include one or more polyamide polymers, stearoxymethicone/dimethicone copolymer, C30-45 alkyl methicone, behenoxyPEG-10 dimethicone, bis-PEG-18methyl ether dimethylsilane, C30-45 alkyl dimethicone, bisPEG-8 dimrthicone, bis-stearyl dimethicone, bis-PEG-12 dimethicone, dimethicone/cyclomethicone/phenyl trimethicone/trimethylsiloxysilicate, polyvinylcaprolactam, trimethylpentanediol/adipic acid/glycerin crosspolymer, bis-PEG-12 dimethicone beeswax, cetearyl alcohol/ceteareth-20, VP/eicosene copolymer, acrylates/octylacrylamide copolymer, VA/crotonates/vinyl neodecanoate copolymer, acrylates copolymer, and vinyl caprolactam/VP/dimethylaminoethyl methacrylate copolymer. Preferably, the one or more BPG is present in the liquid composition in the amount between about 15 wt. % and about 50 wt % (wt % of the entire liquid composition.)

Examples of most preferred base polymer group polymers used herein include polyimide polymers, stearoxymethicone/dimethicone copolymer, dimethicone/cyclomethicone/phenyl trimethicone/trimethylsiloxysilicate, trimethylpentanediol/adipic acid/glycerin crosspolymer, polyvinylcaprolactam, acrylates copolymer and combinations thereof.

The one or more of polysaccharides may be one of carboxy methyl cellulose, alginate, carrageenan, locust bean gum, xanthan gum, sodium hyaluronate, pectin, and mixtures thereof. One preferred category of polysaccharides is carboxy methyl cellulose are those that provide lubricious action when applied to wet skin or other surfaces resulting in flexible films on these surfaces.

The anhydrous solvent must be a solvent in which both the BPG and the polysaccharide can be dispersed in, in the liquid embodiment. To qualify as "anhydrous" for purposes of this invention, the solvent should have no more than 0.1% water. Preferably, in the anhydrous fluid composition the one or more solvent is present in an amount of about 10 wt. % to about 55 wt. % (wt % of the entire liquid composition). Solvents that are suitable for use in the liquid composition include C to C alcohols and isomers thereof, or one or more $C_5$ to $C_{20}$ alkanes or alkenes, or isomers thereof, and combinations of these.

The anhydrous fluid composition may contain a variety of active ingredients such as skin care including polyethylene glycol, laurel lactate/myristyl lactate/cetyl lactate, isostearyl neopentanonte, octyldodecyl sterol stearate, myristyl stearate, caprylic/capric triglyceride, C12-C15 alkyl benzoate, dipentaerythrityl hexacaprylate/hexacaprate, The anhydrous fluid composition may further comprise active agents, cleaning agents, processing aids, or combinations thereof. Preferably, the active agents are therapeutic active agents and comprise one or more of aloe, vitamins, emollients, moisturizers, clotting agents, anti-chafing agents, fragrances, depilatory agents, essential oils, antioxidants, alpha-hydroxy acids, alpha-keto acids, anti-bacterials, anti-fungals, anti-microbials, anti-virals, analgesics, anti-allergenics, antihistamines, anti-inflammatory agents such as superoxide dismutase, anti-irritants, anti-neoplastics, anti-acne agents, anti-aging agents, anesthetics, antiseptics, insect repellents, skin cooling compounds, skin warming compounds, skin protectants, skin penetration enhancers, exfoliants, lubricants, or combinations thereof. Preferably, the cleaning agents comprise de-greasers, surfactants, enzymes, fabric conditioners, anti-microbials, anti-bacterials, anti-fungals, or combinations thereof. Preferably, the processing aids are fillers comprising talc, clay, and diatomaceous earth, or combinations thereof.

When the liquid composition is dried, the result is an anhydrous water sensitive solid film composition containing a base polymer group (BPG) and a polysaccharide, and optionally, one or more additional desired and compatible ingredient (chosen depending on the desired end-use of the film). Preferably, the BPG(s) are present in the amount of 10 wt % to about 50% wt % based on total weight of the anhydrous film. Preferably, the polysaccharide is present in the film in the amount of approximately 5 wt % to 60 wt % based on the total weight of the film. Examples of useful BPGs include one or more polyamides, stearoxymethicone/dimethicone copolymer, bis-PEG-12 dimethicone, dimethicone/cyclomethicone/phenyl trimethicone/trimethylsiloxysilicate, bis-stearyl dimethicone, polyvinylcaprolactam, trimethylpentanediol/adipic acid/glycerin crosspolymer. A particularly useful polysaccharide is carboxy methyl cellulose (CMC). Other active ingredients such as polyethylene glycol for residual effects on surfaces or film modification can be included. By "water sensitive" it is meant the dried film can be eroded or partially solubilized when in contact with water or water vapor.

The preferred base polymer group (BPG) comprises one or more polyamides polymers, stearoxymethicone/dimethicone copolymer, C30-45 alkyl methicone, behenoxyPEG-10 dimethicone, bis-PEG-18methyl ether dimethylsilane, C30-45 alkyl dimethicone, bisPEG-8 dimethicone, bis-stearyl dimethicone, bis-PEG-12 dimethicone, dimethicone/cyclomethicone/phenyl trimethicone/trimethylsiloxysilicate, polyvinylcaprolactam, trimethylpentanediol/adipic acid/glycerin crosspolymer, bis-PEG-12 dimethicone beeswax, cetearyl alcohol/ceteareth-20, VP/eicosene copolymer, acrylates/octylacrylamide copolymer, VA/crotonates/vinyl neodecanoate copolymer, acrylates copolymer, and vinyl caprolactam/VP/dimethylaminoethyl methacrylate copolymer.

The water sensitive, erodible dried film may further comprise active agents, cleaning agents, processing aids, or combinations thereof. Preferably, the active agents are therapeutic active agents and comprise one or more of aloe, vitamins, emollients, moisturizers, clotting agents, anti-chafing agents, fragrances, depilatory agents, essential oils, antioxidants, alpha-hydroxy acids, alpha-keto acids, anti-bacterials, anti-fungals, anti-microbials, anti-virals, analgesics, anti-allergenics, antihistamines, anti-inflammatory agents such as superoxide dismutase, anti-irritants, anti-neoplastics, anti-acne agents, anti-aging agents, anesthetics, antiseptics, insect repellents, skin cooling compounds, skin warming compounds, skin protectants, skin penetration enhancers, exfoliants, lubricants, or combinations thereof. Preferably, the cleaning agents comprise de-greasers, surfactants, enzymes, fabric conditioners, anti-microbials, anti-bacterials, anti-fungals, or combinations thereof. Preferably, the processing aids are fillers comprising talc, clay, and diatomaceous earth, or combinations thereof.

DETAILED DESCRIPTION OF INVENTION

Figure 1:
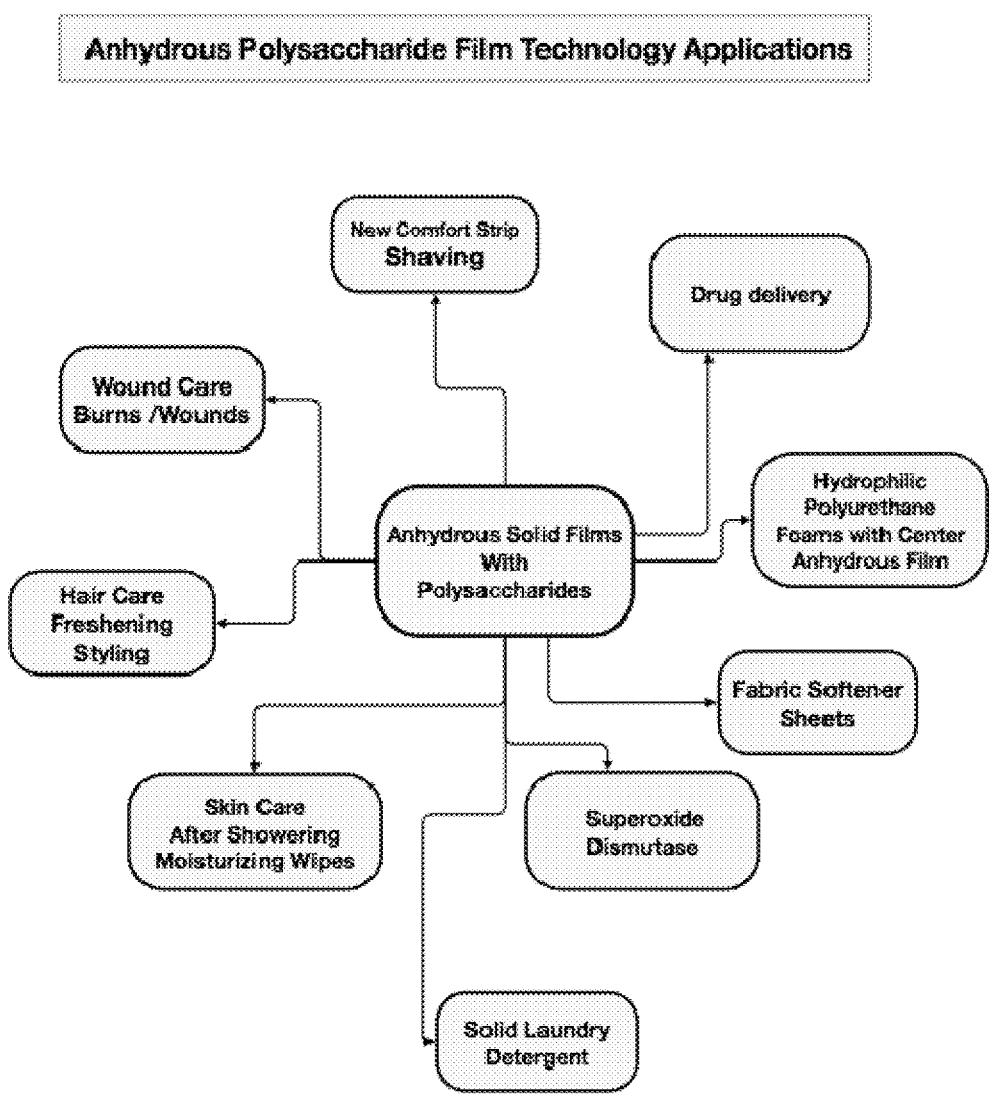
FIG. 1 describes various uses and applications of the embodiments of this invention.
Figure 2:
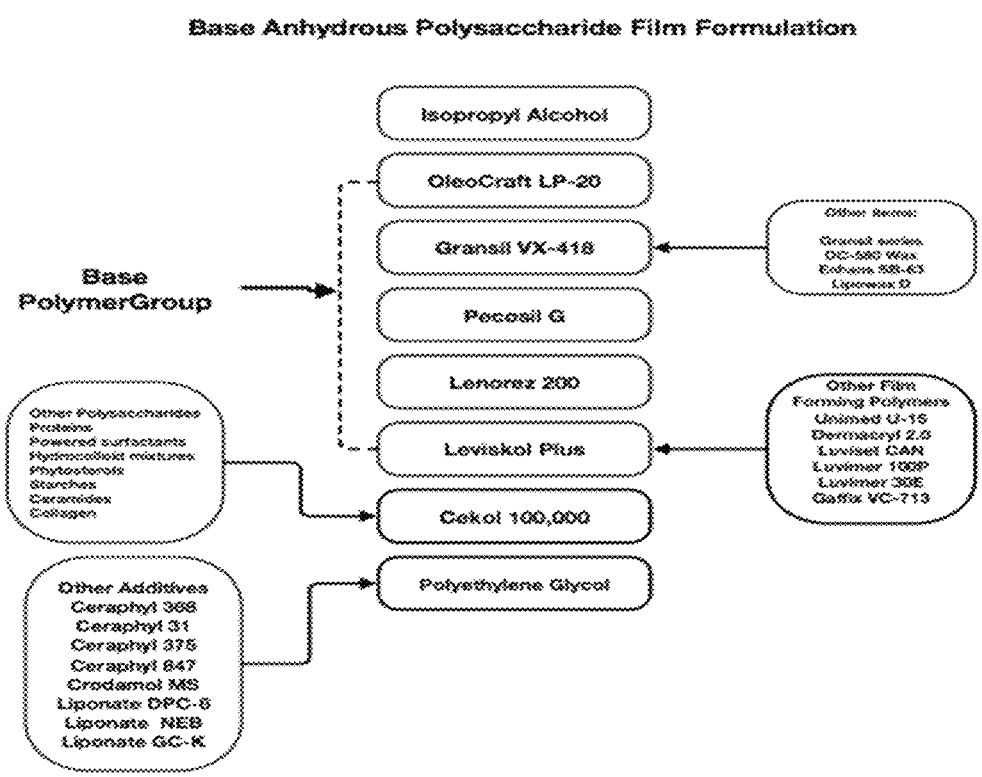
FIG. 2 describes an example of the base anhydrous polysaccharide film formulation. The flexibility of the base anhydrous polysaccharide film formulation is shown in FIG. 2, graphically describing adjustments that can be made in the base polymer group (BPG), variations in polysaccharide types and numerous skin care additives possible. Many other additives are possible depending upon the targeted use for the anhydrous film and the substrates involved.

In the context of shaving implements, the present invention addresses the need for an alternative to PEO by using polysaccharides to provide lubricious and consistent sustained release of one or more active agents through a water sensitive, erodible anhydrous film. The anhydrous films and related embodiments described herein are quite effective in controlling the release rate of polysaccharides and other skin care agents to skin or other surfaces in a variety of applications.

In the presence of a small amount of water and very little pressure, the anhydrous film when contacted against the skin during wet shaving, for example, will deliver instantly consistent and sufficient level of polysaccharide(s) as well as other active agents while maintaining its dimensional and structural integrity.

Utilizing the technology disclosed herein, the anhydrous films can be manufactured in such a way to control the number of uses to deliver satisfactory amounts of polysaccharides or other active agents. For instance, anhydrous films when used as razor comfort strips are envisioned to be effective for about 3 to about 45 uses. Modifying the thickness, composition and size of the anhydrous film allows the number of uses to be delivered by this technology. For instance, the films are contemplated to have a thickness of about 0.1 mm to about 7 mm but can be larger depending upon its product use.

As disclosed herein, the size, thickness and especially the chemical composition can be adjusted for the desired purpose, in a wide variety of unique combinations. The versatility of these anhydrous films will accommodate a continued and consistent amount of polysaccharide film composition released during shaving in addition control the number of shaves the comfort strip can deliver.

The anhydrous film starts out as a fluid composition that may comprise or consist essentially of or consist of a polysaccharide, one or more base polymer group (BPG) polymers, and a sufficient amount of solvent for dispersing the polysaccharide(s) and the other film modifiers depending upon use. Once the base polymer group (BPG) polymers are dispersed in the solvent along with the polysaccharide(s), they are mixed until homogenous along with film modifiers and processed whereupon the solvent is removed to form a substantially uniform dried film comprising or consisting essentially of or consisting of the polysaccharide(s) and the BPG polymer. Additional components such as active agents may be added during the mixing phase to alter rheology or improve resultant film qualities. The dispersion is then cast in a desired thickness and the solvent is removed, leaving a substantially dry film. The film is then cut into desired sizes.

Polysaccharide(s)

Polysaccharides are composed of multiple saccharides (sugars) forming a large, branched or unbranched chain. The vast majority of polysaccharides used in cosmetics are natural or semi-natural. Based on their unique multi-functionality they play a very important role in cosmetic formulation technology. Since polysaccharides are multifunctional they act as thickeners, suspending agents, hair conditioners, moisturizers, emulsifiers, emollients, and even wound-healing agents. Polysaccharides generally are classified based on their electrochemical charges. Carboxy methyl cellulose having a molecular weight of 30,000 to 100,000 disperses in the BPG polymer mix, casts well on release paper and dries with sufficient thickness. This film when wetted or used on wet surface—skin for example—demonstrates a very lubricious, non-sticky feel. *Anionic Polysaccharides: Natural: alginic acid, pectin, xanthan gum, hyaluronic acid, chondroitin sulfate, gum arabic, gum karaya, gum tragacanth Semi-Natural: carboxymethyl-chitin, cellulose gum.

*Cationic Polysaccharides: Natural: chitosan
Semi-Natural: cationic guar gum, cationic hydroxyethylcellulose (HEC).

*Nonionic Polysaccharides: Natural: starch, dextrins, guar gum Semi-Natural: cellulose ethers (e.g. hydroxyethylcellulose, methylcellulose, nitrocellulose).

*Amphoteric Polysaccharides: Semi-Natural: carboxymethylchitosan, N-hydroxy-dicarboxyethyl-chitosan, modified potato starch.

*Hydrophobic Polysaccharides: Semi-Natural: cetyl hydroxyethylcellulose, polyquaternium 24.

The combination of polysaccharide(s) and base polymer group polymers are essential to the function and effectiveness of the resultant films. In the dried film, this combination facilitates the erosion of the base polymer group polymers at a efficient rate, and allows the polysaccharide to be released instantaneously at a consistent and sustained rate. The proper selection of BPG polymers combined with the appropriate polysaccharide forms a uniform mixture when dried. Certain ethyl cellulose polymers (Dow Ethocel) can act as a viscosity modifier in the fluid composition to help make a substantially uniform erodible anhydrous film. Very high levels of polysaccharide (carboxymethyl cellulose, xanthan gum, locust bean gum) can be achieved in these anhydrous compositions—60%.

The fluid composition should have an ideal viscosity level wherein the fluid composition can flow to form a substantially continuous film of substantially uniform thickness. Ideally, viscosity of the fluid composition is between about 800 to about 3000 centipoise (cPs), and more preferably between about 1000 to about 1800 cPs. The viscosity of the anhydrous fluid composition is based upon the amount of anhydrous solvent used together with the type and amount of polysaccharide.

In the fluid composition, the polysaccharide is preferably present in an amount of about 2 wt. % to about 55 wt. %, based on a total weight of the fluid composition. In preferred embodiments of the fluid composition, the polysaccharide is present between about 15 wt. % to about 45 wt. %, and more preferably from about 30 wt. % to about 40 wt. %. After removing the solvent from the fluid composition to form the anhydrous film, the polysaccharide is present in an amount of about 25 wt. % to about 80 wt. %, and more preferably from about 50 wt. % to about 60 wt. %, based on a total weight of the dried anhydrous film. In another embodiment, the polysaccharide is present in the film in an amount of about 20 wt. % to about 70 wt. %.

The molecular weight of the polysaccharide is an important aspect of the intended use of the dried anhydrous film. In general higher molecular weight polysaccharides are preferred for providing lubricious feel on the skin. Furthermore, the final product use will dictate the particle size of the polysaccharide used in the fluid composition. Preferred particle size is through 60 mesh held on 100 mesh (using standard screen sizes). The preferred molecular weight is from 30,000 to 100,000.

Base Polymer Group (BPG) Polymer

The base polymer group of polymers form the basis of providing an anhydrous flexible, non-tacky film when the solvent is removed. It must accommodate and incorporate the polysaccharide ingredient in the fluid state thus providing a uniform mixture or dispersion. Moreover, these group of polymers must be able to accept or disperse a wide variety of active ingredients depending upon desired use of the dry film. The base polymer group generally will provide the dry film to be water sensitive, water soluble, erodible, or water resistant depending upon end use.

The base polymer group (BPG) preferred embodiments of the anhydrous fluid composition consists of one or more polyamide polymers, stearoxymethicone/dimethicone copolymer, C30-45 alkyl methicone, behenoxyPEG-10 dimethicone, bis-PEG-18methyl ether dimethylsilane, C30-45 alkyl dimethicone, bisPEG-8 dimethicone, bis-stearyl dimethicone, bis-PEG-12 dimethicone, dimethicone/cyclomethicone/phenyl trimethicone/trimethylsiloxysilicate, polyvinylcaprolactam, trimethylpentanediol/adipic acid/glycerin crosspolymer, bis-PEG-12 dimethicone beeswax, cetearyl alcohol/ceteareth-20, VP/eicosene copolymer, acrylates/octylacrylamide copolymer, VA/crotonates/vinyl neodecanoate copolymer, acrylates copolymer, and vinyl caprolactam/VP/dimethylaminoethyl methacrylate copolymer. Preferably, the BPG in the liquid composition is in the amount of 15 wt. % to about 50 wt. %

Examples of preferred base polymer group polymers used herein include polyamide polymers—Polyamide-8, stearoxymethicone/dimethicone copolymer, dimethicone/cyclomethicone/phenyl trimethicone/trimethylsiloxysilicate, trimethylpentanediol/adipic acid/glycerin crosspolymer, polyvinylcaprolactam, acrylates copolymer and combinations thereof.

Solvent

The solvent is the essential ingredient to provide the anhydrous fluid phase compositions and serves to assist in forming the films disclosed herein. The solvent should be non-aqueous, and preferably solubilizes the base polymer group polymers. It should not dissolve the polysaccharides, but allows them to be well dispersed in the fluid composition. Additionally, it should be volatile at room temperature, e.g., about 25° Celsius (C), to about 200° C. Preferably, the solvent will be able to dissolve one or more of the processing aids described herein although a dispersion of the processing aids is also acceptable. The solvent is preferably either an alcohol or a hydrocarbon, depending on the choice of base polymer group polymers selected.

Alcohols chosen as the solvent are preferably $C_2$ to $C_{12}$ alcohols or isomers thereof.

Examples include ethanol, propanol, butanol, pentanol, hexanol, heptanol, octanol, nonanol, decanol, undecanol, dodecanol, and their isomers. Preferred alcohols are ethanol, isopropanol, alone or in combination. Hydrocarbon solvents are preferably $C_5$ to $C_{20}$ alkanes, $C_5$ to $C_{20}$ alkenes, or isomers thereof. More preferably, the hydrocarbon solvent is isododecane Preferably, the solvent is present in an amount or quantity sufficient to provide the appropriate and desired consistency to form a substantially continuous film. More preferably, the solvent is present in an amount of about 12 wt. % to about 50 wt. %.

Optional Ingredients

As desired, the fluid composition and resultant anhydrous film can include other components as described herein. An important criteria is that the additional components themselves do not contain water (other than trace amounts), so as to preserve the anhydrous nature of the fluid composition and resultant film.

The anhydrous fluid composition may contain a variety of active ingredients such as skin care including polyethylene glycol, laurel lactate/myristyl lactate/cetyl lactate, isostearyl neopentanonte, octyldodecyl sterol stearate, myristyl stearate, caprylic/capric triglyceride, C12-C15 alkyl benzoate, dipentaerythrityl hexacaprylate/hexacaprate, The anhydrous fluid composition may further comprise active agents, cleaning agents, processing aids, or combinations thereof. Preferably, the active agents are therapeutic active agents and comprise one or more of aloe, vitamins, emollients, moisturizers, clotting agents, anti-chafing agents, fragrances, depilatory agents, essential oils, antioxidants, alpha-hydroxy acids, alpha-keto acids, anti-bacterials, anti-fungals, anti-microbials, anti-virals, analgesics, anti-allergenics, antihistamines, anti-inflammatory agents such as superoxide dismutase, anti-irritants, anti-neoplastics, anti-acne agents, anti-aging agents, anesthetics, antiseptics, insect repellents, skin cooling compounds, skin warming compounds, skin protectants, skin penetration enhancers, exfoliants, lubricants, or combinations thereof. Preferably, the cleaning agents comprise de-greasers, surfactants, enzymes, fabric conditioners, anti-microbials, anti-bacterials, anti-fungals, or combinations thereof. Preferably, the processing aids are fillers comprising talc, clay, and diatomaceous earth, or combinations thereof.

Some preferred embodiments of the fluid composition to make the erodible anhydrous film are shown in Table I below:

The fluid compositions are prepared by charging an appropriate size beaker equipped with a hot plate and mechanical stirrer with the solvent. While stirring, the components of the fluid compositions are added one by one into the solvent until a homogeneous dispersion is achieved. All of the formulations herein were prepared at room temperature (68°-70° F.) except formulation #13 (chart) which had to be heated to 55° F. to assure that particular ingredients are solubilized in the solvent. Preferably, low shear mixing and a cover over the beaker is utilized as each ingredient is added including the polysaccharides to minimize evaporation of the isopropanol. Any of the formulations that are heated are then cooled to room temperature. Skin care agents are added during this time as well. Additional isopropanol is added to replace the amount evaporated during heating and/or adjust the viscosity.

| Ingredients | 1 | 2 | 3 | 4 | 5 | 6 | 7 | 8 | 9 | 10 | 11 | 12 | 13 |
|---|---|---|---|---|---|---|---|---|---|---|---|---|---|
| Isopropol alcohol | 50.33 | 40 | 40 | 40 | 40 | 35 | 35 | 40 | 40 | 35 | 34.79 | 34.22 | 24.22 |
| HSP-1180 | 5 | | | | | | | | | | | | |
| Sylverclear 200 | 5 | 5 | 5 | 5 | | | | | | | | | |
| Advantage Plus | 30 | 30 | 30 | 30 | 10 | 20 | 22 | | | 24 | | | |
| Dow VM-2270 | 4.67 | | | | | | | | | | | | |
| Pecosil G | | 5 | | 5 | 5 | 5 | 5 | 2 | 2 | 4 | 1.74 | 1.74 | 1.74 |
| Cekol 6000 | | 15 | 15 | | | | | | | | | | |
| Cekl 2500 | | | | 15 | | | | | | | | | |
| OleoCraft LP-20 | | | | | 5 | 5 | 5 | 5 | 5 | 5 | 4.35 | 4.35 | 4.35 |
| Lexorez 200 | | | | | 20 | 10 | 10 | 10 | 8 | 10 | 3.48 | 4.05 | 4.05 |
| FC-5002 Resin Gum | | | 5 | | | | | | | | | | |
| C30 Resin Wax | | | | | | 5 | | | | | | | |
| Cekol 5000 | | | | | | 15 | | | | | | | |
| Cekol 30,000 | | | | | | | 15 | 15 | 15 | 15 | 15 | | |
| Luvimer 100P | | | | | | | | 22 | | | | | |
| Luviskol Plus | | | | | | | | | | 24 | 20.87 | 20.87 | 20.87 |
| PEG-200 | 5 | 5 | 5 | 5 | 5 | 5 | 3 | 3 | 3 | 3 | 2.17 | 2.17 | 2.17 |
| Cekol 100,000 | | | | | | | | | | | 30.43 | 30.43 | 30.43 |
| DC-580 Wax | | | | | | | | | | | | 2.17 | |
| Enhans SB-63 | | | | | | | | | | | | | 2.17 |
| Gransil VX-418 | | | | | | | 5 | 3 | 3 | 4 | 2.17 | | |
| Total | 100 | 100 | 100 | 100 | 100 | 100 | 100 | 100 | 100 | 100 | 100 | 100 | 100 |

A stainless steel plate approximately 15"×18" having a thickness of ⅛ inch is covered with a sheet of silicone treated release paper (12"×14") on the top side. Using an appropriate doctor blade, the fluid composition is poured in front of the doctor blade across the paper and drawn down the fluid composition. The cast fluid composition is then dried in a convection oven at about 80° C. to about 85° C. until a constant weight is achieved. Using an appropriate doctor blade, one of ordinary skill in the art can produce dried films having thicknesses of 1 mm, 1.5 mm, or 2 mm. The film should be cooled prior to cutting to desired sizes.

One of skill in the art will have the knowledge to cast the fluid composition onto an appropriate substrate to achieve a film of desired thickness. Substrates contemplated herein include woven and non-woven substrates, hydrophilic polyurethane foam substrates, adhesive backed substrates, polymer substrates, and casting onto a layer of the dried film itself to produce a multi-layered film. The solvent can be removed by heating the cast dispersion in an oven set for a time and temperature sufficient to volatilize the solvent and solidify the film or by other means known to one of ordinary skill in the art.

As an example listed below is formulation #11 listed in the wet or fluid state as well as after drying the cast formulation as described above.

| Ingredients | #11 Fluid | #11 Dry |
|---|---|---|
| Isopropol alcohol | 34.79 | — |
| Pecosil G | 1.74 | 3.30 |
| OleoCraft LP-20 | 4.35 | 8.26 |
| Lexorez 200 | 3.48 | 6.60 |
| Luviskol Plus | 20.87 | 15.85 |
| PEG-200 | 2.17 | 4.12 |
| Cekol 100,000 | 30.43 | 57.75 |
| Gransil VX-418 | 2.17 | 4.12 |
| Total | 100 | 100 |

Technology Applications, Shaving Devices, Product Forms and Methods of Use

The anhydrous films disclosed herein are useful in a variety of applications, such as skin care, hair care, wound care, drug delivery, fabric care such as softening, hydrophilic polyurethane foams containing films, and topical release of superoxide dismutase from specially designed films. Finally, it is possible to design formulations as soluble solid laundry detergents.

Films can be integrated into or associated with a hair removal device, such as razors or razor cartridges. Preferably, the hair removal device is a razor. In the case of a razor, the anhydrous film may be arranged, positioned or otherwise provided on the razor cartridge as a comfort strip. For instance, the comfort strip can be located before and/or after the blade(s) in the direction of cutting and may even be configured as a continuous portion entirely surrounding the blades.

Anhydrous films may be affixed to the hair removal device in any appropriate fashion—it can be mechanically fitted onto a separate razor cartridge, or directly onto the hair removal device. Alternatively, the anhydrous film may be directly or indirectly adhered to the hair removal device by means of an adhesive.

In shaving and hair removal devices, the anhydrous film can controllably and consistently deliver a polysaccharide and/or mixed polysaccharides along with active agents such as shaving aid materials and skin care agents to the skin or hair before, during or after shaving. Once the anhydrous films described herein containing polysaccharides and the active agents are exposed to an adequate amount of water, the polysaccharides along with active agents are released onto the skin or hair as the shaving or hair removal device bearing the film is moved across the skin. As the film moves across the skin, the film solublizes, abrades or erodes away to provide a fresh surface on which the active agents are readily accessible. This is a major improvement over prior art extruded or molded comfort strips wherein the current polyethylene oxide polymer is trapped within a water-insoluble matrix reducing effectiveness. Range of thicknesses can be from 1 mm, 1.5 mm to 2 mm except where the anhydrous film is being coated in a special way such as dots, strips or an ultra thin coating on fabrics for a specific use.

Skin Care Wipe

Another embodiment utilizing the anhydrous polysaccharide film is a dry skin care wipe. The fluid film coated on nonwoven fabric and dried can be used on wet skin after showering before drying off to help dry skin, provide moisturization and protection for the skin. When the films are in the form of an impregnated skin care wipe, a user sweeps the wipe across either wet skin or activates the wipe with water to moisten the film just prior to use, so that water-soluble active agents within the wipe, including polysaccharides, are released onto the skin in the area desired. For instance, such a wipe may comprise an adjusted silicone polymer mix with one or more skin care active ingredients such as emollient esters, glycerin, and a specially designed fragrance along with one or more polysaccharides capable of forming a supple, non-tacky protective film. The polysaccharide level in the dry film can be about 10 wt. % to about 60 wt. %.

Hair Care Styling/Freshening

Yet another embodiment of the erodible anhydrous film contemplates hair care wherein a comb or brush comprises the film disclosed herein. The anhydrous film is cast or molded into strips or strings for wrapping around the comb or brush "teeth", or form the actual "teeth" itself. A user then runs the comb through wet hair so that water-soluble active agents within the film associated or attached to the comb/brush, including polysaccharides to provide slip and body to the hair surface. Alternatively, the user can activate the film with an adequate amount of water and run the comb through dry hair. Fluid compositions can have an adjusted base polymer group containing specific polysaccharides in an amount of about 5 wt. % to 12 wt. %. Vinyl caprolactam or mixed arcylates are specifically designed for hair care use and can be easily incorporated into the base polymer group along with selected fragrances or other special hair treatments.

Wound Care

Because their biocompatibility, biodegradability and similarity to macromolecules recognized by the human body, natural polymers such as polysaccharides (alginates, chitin, chitosan, heparin, chondroitin), proteoglycans and proteins (collagen, gelatin, fibrin, keratin, silk fibroin, egg-shell membrane) are extensively used in wounds and burns management. Fluid formulation can be adjusted to include appropriate pharmaceutical grade polysaccharide. Formulations can include base polymer group polymers that contain silicone polymers that can provide cleansing, skin protection and items such as clotting agents to stop bleeding along with appropriate polysaccharide such as carboxyl methyl cellulose. Fluid formulations can be coated on nonwoven substrates or hydrophilic polyurethane foam sheet stock. Film modifying aids such as glycerin and glycerin polymers can be included for burn treatment.

Drug Delivery

Fluid compositions can be designed specifically incorporating base polymer group polymers along with polysaccharides plus drugs for acne treatment such as salicylic acid, benzoyl peroxide coated and dried on nonwoven fabrics or gauze material forming pads or wipes. Patient would activate by moistening with water and wiping across affected skin area leaving a dry treatment film. Other drug medication wipes including steroids, antibacterial agents can be accommodated.

Hydrophilic Polyurethane Impregnated Foams

Another embodiment of the skin care wipes comprises incorporating the fluid composition into or onto a foam sheet to form the anhydrous film. As an example of such an embodiment, a hydrophilic polyurethane foam (HPU) sheet having recesses on at least one surface of the HPU sheet, may be filled with the fluid composition described herein. The HPU can be made up of a water phase and a polymer phase that is mixed together to make a foam in a mold so as to form the recesses. This fluid composition can be cast into the foam sheet settling into the recesses and dried to remove the isopropanol solvent. Alternatively, the foam sheet can be saturated with the fluid composition and dried such that the anhydrous film resides on a surface of the foam sheet and/or in the interstitial spaces of the foam sheet.

Fabric Softeners

In the area of fabric care, another embodiment of the erodible anhydrous film may also be used in the form of or in connection with a dryer sheet. The anhydrous film may be used in treating or softening a fabric in a dryer, where the fabric is contacted with the dryer sheet, in a dryer, under conditions of heat and water vapor. For instance, the dryer sheet can comprise of the anhydrous film of the general formula as described above wherein base polymer group polymer, and additionally about 10 wt. % of mixed solid fabric softener ingredients, fragrance and solid nonionic surfactants, and diatomaceous earth.

Solid Laundry Detergent

The fluid composition may be cast onto release paper substrate. As a laundry detergent film, the film in the presence of water, will solubilize releasing fabric cleaning agents into the wash water in a laundry machine during operation. Such a laundry detergent film can include a concentrated water soluble detergent suitable for use in a standard or high efficiency washing machine. For instance, the laundry detergent film can be an anhydrous film of the general formula as described above, but with a minimum amount of base polymer group polymer. Preferably, the base polymer group polymer is water soluble, and can comprise a PVP polymer. The formula can also contain polysaccharide in an amount of about 10 wt. %, as well as laundry detergent ingredients comprising surfactants, enzymatic cleaners, fabric brighteners, fragrance, and the like.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

The invention claimed is:

1. An anhydrous fluid composition for forming a film comprising
    a polysaccharide selected from the group consisting of carboxy methyl cellulose, alginate, carrageenan, locust bean gum, xanthan gum, sodium hyaluronate, pectin, and mixtures thereof, present in an amount of about 15 wt. % to about 45 wt. %,
    a base polymer group polymer selected from the group consisting of
        polyvinylcaprolactam,
        vinylpyrrolidone/eicosane copolymer,
        acrylates/octylacrylamide copolymer,
        vinylacetate/crotonates/vinyl neodecanoate copolymer, and
        vinyl caprolactam/vinylpyrrolidone/dimethylaminoethyl methacrylate copolymer, present in an amount of about 15 wt. % to about 50 wt. %; and
    one or more anhydrous solvents present in an amount of about 10 wt. % to about 55 wt. %, and wherein the one or more solvent comprises one or more $C_2$ to $C_{12}$ alcohols and isomers thereof, one or more $C_5$ to $C_{20}$ alkanes and isomers thereof, or $C_5$ to $C_{20}$ alkenes, and isomers thereof,
    wherein said anhydrous fluid composition forms a film when said solvent is removed.

2. The anhydrous fluid composition of claim 1 further comprising an anti-acne active agent film modifying aids, cleaning agents, processing aids, or combinations thereof.

3. The anhydrous fluid composition of claim 1 further comprising water in an amount of about less than 0.05 wt. %, based on a total weight of said anhydrous fluid composition.

4. An erodible anhydrous film comprising
    a polysaccharide selected from the group consisting of carboxy methyl cellulose, alginate, carrageenan, locust bean gum, xanthan gum, sodium hyaluronate, pectin, and mixtures thereof, in an amount of about 20 wt. % to about 70 wt. % based on a total weight of said erodible anhydrous film;
    and an erodible a base polymer group polymer selected from the group consisting of
        polyvinylcaprolactam,
        vinylpyrrolidone/eicosane copolymer,
        acrylates/octylacrylamide copolymer,
        vinylacetate/crotonates/vinyl neodecanoate copolymer, and
        vinyl caprolactam/vinylpyrrolidone/dimethylaminoethyl methacrylate copolymer, in an amount of about 10 wt. % to about 50 wt. %.

5. The erodible anhydrous film of claim 4 further comprising an anti-acne active agent, cleaning agents, film modifying aids, or combinations thereof.

6. The erodible anhydrous film of claim 5 wherein the film modifying aids are plasticizers selected from the group consisting of polyethylene glycol, propylene glycol, butylene glycol, pentalene glycol, glycerin or combinations thereof.

7. The anhydrous film of claim 4 further including a substrate.

8. The anhydrous film of claim 7, which is a skin care, a wound care device, a hair care device or a fabric care device.

9. The erodible anhydrous film of claim 4, which is an erodible shaving aid material that further comprises a therapeutic agent selected from the group consisting of aloe, vitamins, emollients, moisturizers, anti-chafing agents, depilatory agents, essential oils, antioxidants, alpha-hydroxy acids, alpha-keto acids, anti-bacterials, anti-fungals, anti-microbials, anti-virals, analgesics, anti-allergenics, antihistamines, anti-inflammatory agents, anti-irritants, anti-acne agents, anesthetics, exfoliants, and combinations thereof.

10. The erodible anhydrous film of claim 9 wherein said anhydrous film further includes film modifying aids, or combinations thereof.

11. A hair removal device comprising the anhydrous film which is an erodible shaving aid material of claim 9.

12. The anhydrous fluid composition of claim 1, wherein the polysaccharide is carboxy methyl cellulose.

13. The anhydrous fluid composition of claim 1, wherein the polysaccharide is present in an amount of about 30% wt to about 40% wt.

14. The anhydrous fluid composition of claim 1, which comprises
  isopropyl alcohol as an anhydrous solvent,
  polyvinyl caprolactam as the film forming polymer,
  carboxy methyl cellulose as the polysaccharide,
and further comprises
  polyamide-8,
  bis-stearyl dimethicone,
  dimethicone/cyclomethicone/phenyl trimethicone/trimethylsiloxysicate
  trimethylpentanediol/adipic acid/glycerin crosspolymer, and
  polyethylene glycol.

* * * * *